United States Patent
Nampoothiri et al.

(10) Patent No.: US 6,680,186 B2
(45) Date of Patent: Jan. 20, 2004

(54) NUCLEOTIDE SEQUENCES WHICH ENCODE PLSC GENE

(75) Inventors: Madhavan Nampoothiri, Kerala (IN); Brigitte Bathe, Salzkotten (DE); Lothar Eggeling, Juelich (DE); Hermann Sahm, Juelich (DE)

(73) Assignees: Degussa AG, Duesseldorf (DE); Forschungszentrum Juelich GmbH, Juelich (DE)

( * ) Notice: Subject to any disclaimer, the term of this patent is extended or adjusted under 35 U.S.C. 154(b) by 0 days.

(21) Appl. No.: 09/829,931

(22) Filed: Apr. 11, 2001

(65) Prior Publication Data

US 2003/0003558 A1 Jan. 2, 2003

(30) Foreign Application Priority Data

Jul. 1, 2000 (DE) .......................... 100 32 173

(51) Int. Cl.[7] .............................. C12N 9/10; C12N 1/20; C12P 21/04; C12P 13/04; C07H 21/04
(52) U.S. Cl. .................. 435/193; 435/6; 435/252.3; 435/71.1; 435/370.1; 435/252.32; 435/320.1; 435/106; 435/110; 435/115; 536/23.2; 536/23.1
(58) Field of Search ................ 435/193, 106, 435/6, 252.3, 370.1, 252.32, 32.01, 110, 115, 71.1; 536/23.2, 23.1

(56) References Cited

U.S. PATENT DOCUMENTS 4,965,197 A * 10/1990 Liebl et al. ................ 435/69.8

FOREIGN PATENT DOCUMENTS

| DE | 196 44 567 | 4/1998 |
| EP | 0 358 940 | 3/1990 |
| EP | 1 106 694 | 6/2001 |
| EP | 1108790 A2 | 6/2001 |
| WO | WO 01/00805 | 6/2000 |
| WO | WO 01/00802 | 1/2001 |
| WO | WO 01/00805 | 1/2001 |
| WO | WO 01/00844 | 1/2001 |

OTHER PUBLICATIONS

Lee et al. Characterizationof glk, a gene coding for glucose kinase of *corynebacterium glutamicum*. Abstracts of the General Meeting of the American Society for Microbiology, (1999) vol. 99, pp. 369.*

Park et al. Characterization of glk, a gene coding for glucose kinase of *Corynebacterium glutamicum*. FEMS Microbiology Letters, vol. 188, pp. 209–215 (2000).*

Park et al. GenEmbl database—Accession #0 AF096280 (2000).*

Coleman. Characterization of the *Escherichia coli* gene for 1–acyl–sn–glycerol–3–phosphate acyltransferase (plsC). Mol. Gen. Genet. vol. 232, pp. 295–303 (1992).*

Sun–Yang Park, et al., FEMS Microbiology Letters, vol. 188, No. 2, pp. 209–215, "Characterization of glk, a Gene Coding for Glucose Kinase of *Corynebacterium glutamicum*", 2000.

Derwent Publications, AN 1993–256072, KR 9 208 381, Sep. 26, 1992.

M. Clark, et al., Database EMBL, AN AW305676, pp. 1–2, XP–002185711, "Washu Zebrafish Est Project 1998", Jan. 21, 2000.

(List continued on next page.)

*Primary Examiner*—Ponnathapu Achutamurthy
*Assistant Examiner*—Yong Pak
(74) *Attorney, Agent, or Firm*—Oblon, Spivak, McClelland, Maier & Neustadt, P.C.

(57) ABSTRACT

The present invention relates to polynucleotides corresponding to the plsC gene and which encode 1-acyl-SN-glycerol-3-phosphate acyltransferase, methods of producing L-amino acids, and methods of screening for polynucleotides which encode proteins having 1-acyl-SN-glycerol-3-phosphate acyltransferase activity.

51 Claims, 1 Drawing Sheet

OTHER PUBLICATIONS

B. Birren, et al., Database EMBL, AN AC012238, pp. 1–49, XP–002185709, "*Homo sapiens,* Clone RP11–16F4", Oct. 22, 1999.

National Center Institute, Cancer Genome Anatomy Project, Database EMBL, AN AI970295, pp. 1–2, XP–002185710, "Tumor Gene Index http://www.ncbi.nlm.nih.gov/ncicgap", Aug. 26, 1999.

Derwent Publications, AN 2001–061975, WO 01 00844, Jan. 4, 2001.

Derwent Publications, AN 2001–071486, WO 01 00805, Jan. 4, 2001.

* cited by examiner

NUCLEOTIDE SEQUENCES WHICH ENCODE PLSC GENE

BACKGROUND OF THE INVENTION

1. Field of the Invention

The present invention relates to polynucleotides corresponding to the plsC gene and which encode 1-acyl-SN-glycerol-3-phosphate acyltransferase, methods of producing L-amino acids, and methods of screening for polynucleotides which encode proteins having 1-acyl-SN-glycerol-3-phosphate acyltransferase activity.

2. Discussion of the Background

Amino acids, particularly L-lysine and L-glutamate, are used in human medicine, in the pharmaceutical industry, in the food industry, and are used in particular in animal nutrition.

It is known that amino acids are produced by the fermentation of strains of coryneform bacteria, particularly *Corynebacterium glutamicum*. Due to the considerable importance of these amino acids, attempts are continuously being made to improve the production process. Process improvements can involve fermentation technology measures, such as stirring and supplying with oxygen for example, or can relate to the composition of the culture media, such as the sugar concentration during fermentation for example, or to work-up to give the desired form of product by ion exchange chromatography for example, or to the intrinsic production properties of the microorganism itself.

Methods of mutagenesis, selection and mutant selection are employed in order to improve the production properties of these microorganisms. In this manner, strains are obtained which are resistant to antimetabolites, such as the lysine analogon S-(2-aminoethyl)-cysteine for example, or which are auxotrophic for metabolites of regulatory importance, and which produce L-amino acids such as L-lysine or L-glutamate for example.

Moreover, for some years methods of recombinant DNA technology have been used to improve strains of Corynebacterium which produce amino acids. This has been achieved by amplifying individual amino acid biosynthesis genes and investigating the effect on amino acid production. Review articles on this topic, amongst other sources, are those by Kinoshita ("Glutamic Acid Bacteria", in: Biology of Industrial Microorganisms, Demain and Solomon (Eds.), Benjamin Cummings, London, UK, 1985, 115–142), Hilliger (BioTec 2, 40–44 (1991)), Eggeling (Amino Acids 6:261–272 (1994)), Jetten and Sinskey (Critical Reviews in Biotechnology 15, 73–103 (1995)) and Sahm et al. (Annals of the New York Academy of Science 782, 25–39 (1996)).

However, there remains a critical need for improved methods of producing L-amino acids and thus for the provision of strains of bacteria producing higher amounts of L-amino acids. On a commercial or industrial scale even small improvements in the yield of L-amino acids, or the efficiency of their production, are economically significant. Prior to the present invention, it was not recognized that enhancement or over-expression of the plsC gene, encoding 1-acyl-SN-glycerol-3-phosphate acyltransferase, would improve L-amino acid yields.

SUMMARY OF THE INVENTION

One object of the present invention, is providing a new process adjuvant for improving the fermentative production of L-amino acids, particularly L-lysine and L-glutamate. Such process adjuvants include enhanced bacteria, preferably enhanced coryneform bacteria which express high amounts of 1-acyl-SN-glycerol-3-phosphate acyltransferase which is encoded by the plsC gene.

Thus, another object of the present invention is providing such an enhanced bacterium, which expresses an enhanced amount of 1-acyl-SN-glycerol-3-phosphate acyltransferase or gene products of the plsC gene.

Another object of the present invention is providing a bacterium, preferably a coryneform bacterium, which expresses a polypeptide that has an enhanced 1-acyl-SN-glycerol-3-phosphate acyltransferase.

Another object of the invention is to provide a nucleotide sequence encoding a polypeptide which has 1-acyl-SN-glycerol-3-phosphate acyltransferase sequence. One embodiment of such a sequence is the nucleotide sequence of SEQ ID NO: 1.

A further object of the invention is a method of making 1-acyl-SN-glycerol-3-phosphate acyltransferase or an isolated polypeptide having a 1-acyl-SN-glycerol-3-phosphate acyltransferase activity, as well as use of such isolated polypeptides in the production of amino acids. One embodiment of such a polypeptide is the polypeptide having the amino acid sequence of SEQ ID NO: 2.

Other objects of the invention include methods of detecting nucleic acid sequences homologous to SEQ ID NO: 1, particularly nucleic acid sequences encoding polypeptides that have 1-acyl-SN-glycerol-3-phosphate acyltransferase activity, and methods of making nucleic acids encoding such polypeptides.

The above objects highlight certain aspects of the invention. Additional objects, aspects and embodiments of the invention are found in the following detailed description of the invention.

DETAILED DESCRIPTION OF THE INVENTION

Figure 1:
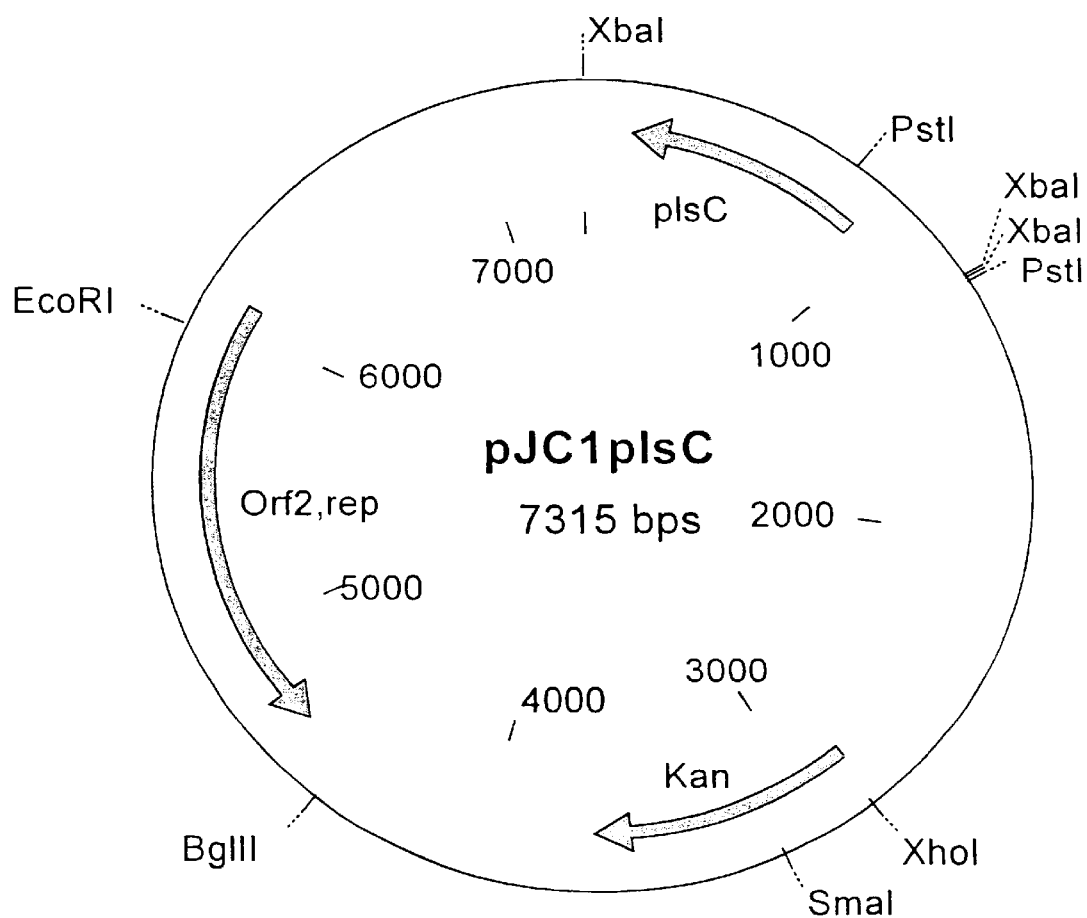
FIG. 1: Map of the plasmid pJC1plsC

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory, New York (1982) and Sambrook et al., Molecular Cloning: A Laboratory Manual, Cold Spring Harbor Laboratory, New York (1989) and the various references cited therein.

Amino acids, particularly L-lysine and L-glutamate, are used in human medicine, in veterinary medicine, in the pharmaceutical industry and particularly in the food industry. There is therefore a general interest in the provision of new, improved processes for producing amino acids, particularly L-glutamate.

When L-lysine or lysine or L-glutamate or glutamate are mentioned below, this means not only the bases but also the salts thereof.

The present invention relates to a coryneform bacterium, in which the plsC gene thereof, which encodes 1-acyl-SN-glycerol-3-phosphate acyltransferase, is enhanced.

In this connection, the term "enhancement" means increasing the intracellular activity of one or more enzymes in a microorganism which are encoded by the corresponding DNA.

Enhancement can be achieved with the aid of various manipulations of the bacterial cell.

In order to achieve enhancement, particularly overexpression, the number of copies of the corresponding gene can be increased, a strong promoter can be used, or the promoter- and regulation region or the ribosome binding site which is situated upstream of the structural gene can be mutated. Expression cassettes which are incorporated upstream of the structural gene act in the same manner. In addition, it is possible to increase expression in the course of the fermentative production of L-lysine- or L-glutamate by employing inducible promoters. A gene can also be used which encodes a corresponding enzyme with a high activity. Expression can also be improved by measures for extending the life of the m-RNA. Furthermore, enzyme activity as a whole is increased by preventing the degradation of the enzyme. Moreover, these measures can optionally be combined in any desired manner.

Additionally, a strong promoter can be used, or the promoter- and regulation region or the ribosome binding site which is situated upstream of the structural gene can be engineered or mutated. Expression cassettes which are incorporated upstream of the structural gene act in the same manner.

Similarly, it is possible to increase gene expression in the course of the fermentative production of an amino acid, such as L-lysine- or L-glutamate by employing inducible promoters.

A gene can also be used which encodes a corresponding or variant enzyme with a high activity. Preferably the corresponding enzyme has a greater activity than the native form of the enzyme, more preferably at least in the range of 5, 10, 25% or 50% more activity, most preferably more than twice the activity of the native enzyme.

Expression can also be improved by measures for extending the life of the m-RNA.

Furthermore, enzyme activity as a whole can be increased by preventing the degradation of the expressed enzyme. Moreover, these measures can optionally be combined in any desired manner.

The microorganisms to which the present invention relates can produce L-amino acids, particularly L-lysine and L-glutamate, from glucose, saccharose, lactose, fructose, maltose, molasses, starch or cellulose, or from glycerol and ethanol. They can be representatives of coryneform bacteria, particularly of the genus Corynebacterium. A bacterium of the genus Corynebacterium which should be mentioned in particular is the *Corynebacterium glutamicum* species, which is known to those skilled in the art for its capacity of producing L-amino acids.

Examples of suitable strains of the genus Corynebacterium, particularly of the *Corynebacterium glutamicum* species, are the known wild-type strains

*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869, and
*Brevibacterium divaricatum* ATCC14020,
and L-lysine-producing mutants or strains which are produced therefrom, such as
*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464, and
*Corynebacterium glutamicum* DSM5715.

Preferably, a bacterial strain enhanced for expression of a plsC-like gene that encodes a polypeptide with 1-acyl-SN-glycerol-3-phosphate acyltransferase activity, will improve amino acid yields at least 1%.

In the context of the present Application, a polynucleotide sequence is "homologous" with the sequence according to the invention if at least 70%, preferably at least 80%, most preferably at least 90% of its base composition and base sequence corresponds to the sequence according to the invention. According to the invention, a "homologous protein" is to be understood to comprise proteins which contain an amino acid sequence at least 70% of which, preferably at least 80% of which, most preferably at least 90% of which, corresponds to the amino acid sequence which is encoded by the plsC gene (SEQ ID No. 1), wherein "corresponds" is to be understood to mean that the corresponding amino acids are either identical or are mutually homologous amino acids. The expression "homologous amino acids" denotes those which have corresponding properties, particularly with regard to their charge, hydrophobic character, steric properties, etc.

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482–489 (1981), to find the best segment of identity or similarity between two sequences. Gap performs global alignments: all of one sequence with all of another similar sequence using the method of Needleman and Wunsch, J. Mol. Biol. 48:443–453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The present invention also relates to a polynucleotide as described above, which is preferably a replicable DNA containing:
  (i) the nucleotide sequence shown in SEQ ID No. 1, or
  (ii) at least one sequence which corresponds to sequence (i) in the context of the degeneracy of the genetic code, or (iii) at least one sequence which hybridizes with the sequence complementary to sequence(i) or (ii), and optionally (iv) functionally neutral mutations in (i) which result in the same or a homologous amino acid.

The present invention further relates to a replicable polynucleotide which comprises or consists of the nucleotide sequence of SEQ ID No. 2, a polynucleotide sequence which encodes a polypeptide which comprises or consists of the amino acid sequence of SEQ ID No. 2, a vector containing the DNA sequence of *C. glutamicum* which encodes the plsC gene, contained in the vector (plasmid) pJC1plsC deposited as a *Corynebacterium glutamicum* with the number DSM 13492, and coryneform bacteria which serve as a host cell and which contain the vector or in which the plsC gene is enhanced.

The present invention also relates to polynucleotides which contain the complete gene with the polynucleotide sequence corresponding to SEQ ID No. 1 or fragments thereof, and which can be obtained by screening by means of the hybridization of a corresponding gene bank with a probe which contains the sequence of said polynucleotide corresponding to SEQ ID No. 1 or a fragment thereof, and isolation of said DNA sequence.

Polynucleotide sequences according to the invention are suitable as hybridization probes for RNA, cDNA and DNA, in order to isolate the complete length of cDNA which encodes 1-acyl-SN-glycerol-3-phosphate acyltransferase and in order to isolate those cDNAs or genes which exhibit a high degree of similarity to the sequence of the 1-acyl-SN-glycerol-3-phosphate acyltransferase gene.

Polynucleotide sequences according to the invention are also suitable as primers for polymerase chain reaction (PCR) for the production of DNA which encodes 1-acyl-SN-glycerol-3-phosphate acyltransferase.

Oligonucleotides such as these, which serve as probes or primers, can contain more than 30, preferably up to 30, more preferably up to 20, most preferably at least 15 successive nucleotides. Oligonucleotides with a length of at least 40 or 50 nucleotides are also suitable.

The term "isolated" means separated from its natural environment.

The term "polynucleotide" refers in general to polyribonucleotides and polydeoxyribonucleotides, and can denote an unmodified RNA or DNA or a modified RNA or DNA.

The term "polypeptides" is to be understood to mean peptides or proteins which contain two or more amino acids which are bound via peptide bonds.

The polypeptides according to invention include polypeptides corresponding to SEQ ID No. 2, particularly those with the biological activity of 1-acyl-SN-glycerol-3-phosphate acyltransferase, and also includes those, at least 70% of which, preferably at least 80% of which, are homologous with the polypeptide corresponding to SEQ ID No. 2, and most preferably those which exhibit a homology of least 90% to 95% with the polypeptide corresponding to SEQ ID No. 2 and which have the cited activity.

The invention also relates to a process for the fermentative production of L-amino acids, particularly L-lysine and L-glutamate, using coryneform bacteria which in particular already produce an amino acid and in which the nucleotide sequences which encode the plsC gene are enhanced, and in particular are over-expressed.

In the present invention, the plsC gene of *C. glutamicum* which encodes 1-acyl-SN-glycerol-3-phosphate acyltransferase (EC 2.3.1.51) is demonstrated for the first time.

In order to isolate the plsC gene or other genes of *C. glutamicum*, a gene bank of this microorganism is first of all constructed in *E. coli*. The construction of gene banks is described in generally known textbooks and handbooks. Examples thereof include the textbook by Winnacker: Gene und Klone, Eine Einführung in die Gentechnologie (Verlag Chemie, Weinheim, Germany, 1990) or the Handbook by Sambrook et al.: Molecular Cloning, A Laboratory Manual (Cold Spring Harbor Laboratory Press, 1989). One very well known gene bank is that of the *E. coli* K-12 strain W3110, which was constructed by Kohara et al. (Cell 50, 495–508 (1987)) in λ-vectors. Bathe et al. (Molecular and General Genetics, 252:255–265, 1996) described a gene bank of *C. glutamicum* ATCC13032, which with the aid of the cosmid vector SuperCos I (Wahl et al., 1987, Proceedings of the National Academy of Sciences USA, 84:2160–2164) was constructed in the *E. coli* K-12 strain NM554 (Raleigh et al., 1988, Nucleic Acids Research 16:1563–1575. Bormann et al. (Molecular Microbiology 6(3), 317–326 (1992)) in turn describe a gene bank of *C. glutamicum* ATCC13032 using the cosmid pHC79 (Hohn and Collins, Gene 11, 291–298 (1980)). Plasmids such as pBR322 (Bolivar, Life Sciences, 25, 807–818 (1979)) or pUC9 (Vieira et al., 1982, Gene, 19:259–268) can also be used for the production of a gene bank of *C. glutamicum* in *E. coli*. Those *E. coli*-strains which are restriction- and recombination-deficient are particularly suitable as hosts. One example thereof is the strain DH5αmcr, which was described by Grant et al. (Proceedings of the National Academy of Sciences USA, 87 (1990) 4645–4649). Long DNA fragments which are cloned with the aid of cosmids can subsequently again be subcloned in common vectors which are suitable for sequencing and can then be sequenced, as described by Sanger et al. (Proceedings of the National Academy of Sciences of the United States of America, 74:5463–5467, 1977).

In this manner, a new DNA sequence of *C. glutamicum* has been obtained which encodes the plsC gene and which as SEQ ID No. 1 forms part of the present invention. Moreover, the amino acid sequence of the corresponding protein has been derived from the present DNA sequence using the methods described above. The resulting amino acid sequence of the plsC gene product is illustrated in SEQ ID No. 2.

The invention also relates to coding DNA sequences which result from SEQ ID No. 1 by degeneration of the genetic code. In the same manner, the invention further relates to DNA sequences which hybridize with SEQ ID No. 1 or with parts of SEQ ID No. 1. Moreover, one skilled in the art is also aware of conservative amino acid replacements such as the replacement of glycine by alanine or of aspartic acid by glutamic acid in proteins as "sense mutations" which do not result in any fundamental change in the activity of the protein, i.e. which are functionally neutral. It is also known that changes at the N- and/or C-terminus of a protein do not substantially impair the function thereof, and may even stabilise said function. Amongst other sources, one skilled in the art will find information on this topic in the articles by Ben-Bassat et al. (Journal of Bacteriology 169:751–757 (1987)), by O'Regan et al. (Gene 77:237–251 (1989)), by Sahin-Toth et al. (Protein Sciences 3:240–247 (1994)), by Hochuli et al. (Bio/Technology 6:1321–1325 (1988)) and in known textbooks on genetics and molecular biology. The present invention also relates to amino acid sequences which result in a corresponding manner from SEQ ID No. 2.

In the same manner, the present invention also relates to DNA sequences which hybridize with SEQ ID No. 1 or with parts of SEQ ID No. 1. Finally, the present invention relates to DNA sequences which are produced by polymerase chain reaction (PCR) using oligonucleotide primers which result from SEQ ID No. 1. Oligonucleotides of this type typically have a length of at least nucleotides.

Amongst other sources, one skilled in the art will find instructions for the identification of DNA sequences by means of hybridization in the Handbook "The DIG System User's Guide for Filter Hybridization" published by Boehringer Mannheim GmbH (Mannheim, Germany, 1993) and in the article by Liebl et al. (International Journal of Systematic Bacteriology (1991) 41: 255–260). Amongst other sources, one skilled in the art will find instructions for the amplification of DNA sequences with the aid of polymerase chain reaction (PCR) in the Handbooks by Gait: Oligonucleotides synthesis: a practical approach (IRL Press, Oxford, UK, 1984) and by Newton and Graham: PCR (Spektrum Akademischer Verlag, Heidelberg, Germany, 1994).

The work which has been carried out on the present invention has enabled it to be ascertained that, after enhancement of their plsC genes has been effected, coryneform bacteria produce amino acids, particularly L-lysine and L-glutamate, in an improved manner.

The genes or gene constructs concerned can either be present with different numbers of copies in plasmids, or can be integrated and amplified in the chromosome. Alternatively, over-expression of the gene concerned can be effected by changing the composition of the medium and by changing the way in which cultivation is effected.

Amongst other sources, one skilled in the art will find instructions on this topic in the articles by Martin et al. (Bio/Technology 5, 137–146 (1987)), by Guerrero et al. (Gene 138, 35–41 (1994)), by Tsuchiya and Morinaga (Bio/Technology 6, 428–430 (1988)), by Eikmanns et al. (Gene 102, 93–98 (1991)), in European Patent Specification EPS 0 472 869, in U.S. Pat. No. 4,601,893, in the articles by Schwarzer and Puhler (Bio/Technology 9, 84–87 (1991), by Reinscheid et al. (Applied and Environmental Microbiology 60, 126–132 (1994)), by LaBarre et al. (Journal of Bacteriology 175, 1001–1007 (1993)), in Patent Application WO 96/15246, in the article by Malumbres et al. (Gene 134, 15–24 (1993)), in Japanese laid-open Patent Specification JP-A-10-229891, in the articles by Jensen and Hammer (Biotechnology and Bioengineering 58, 191–195 (1998)), by Makrides (Microbiological Reviews 60:512–538 (1996)) and in known textbooks on genetics and molecular biology.

For example, the plsC gene according to the invention has been over-expressed with the aid of plasmids.

Suitable plasmids are those which are replicated and expressed in coryneform bacteria. Numerous known plasmid vectors such as pZ1 (Menkel et al., Applied and Environmental Microbiology (1989) 64: 549–554), pEKEx1 (Eikmanns et al., Gene 102:93–98 (1991)) or pHS2-1 (Sonnen et al., Gene 107:69–74 (1991)) are based on the cryptic plasmids pHM1519, pBL1 or pGA1. Other plasmid vectors, such as those which are based on pCG4 (U.S. Pat. No. 4,489,160), or pNG2 (Serwold-Davis et al., FEMS Microbiology Letters 66, 119–124 (1990)), or pAG1 (U.S. Pat. No. 5,158,891), can be used in the same manner.

One example of a plasmid with the aid of which the plsC gene can be over-expressed is pJC1plsC (FIG. 1), which is based on the E. coli-C. glutamicum shuttle vector pJC1 (Cremer et al., 1990, Molecular and General Genetics 220: 478–480) and which contains the DNA sequence of C. glutamicum which encodes the plsC gene. This is contained in the strain DSM5715/pJC1plsC.

Also suitable are those plasmid vectors by means of which the process of gene amplification by integration in the chromosome can be employed, such as that described, for example, by Reinscheid et al. (Applied and Environmental Microbiology 60, 126–132 (1994)) for the duplication or amplification of the hom-thrb operon. In this method, the complete gene is cloned in a plasmid vector which can replicate in a host (typically E. coli), but which cannot replicate in C. glutamicum. Examples of suitable vectors include pSUP301 (Simon et al., Bio/Technology 1, 784–791 (1983)), pK18mob or pK19mob (Schäfer et al., Gene 145, 69–73 (1994)), pGEM-T (Promega Corporation, Madison, Wis., USA), pCR2.1-TOPO (Shuman (1994). Journal of Biological Chemistry 269:32678–84; U.S. Pat. No. 5,487, 993), pCR®Blunt (Invitrogen, Groningen, Holland; Bernard et al., Journal of Molecular Biology, 234: 534–541 (1993)) or pEM1 (Schrumpf et al, 1991, Journal of Bacteriology 173:4510–4516). The plasmid vector which contains the gene to be amplified is subsequently converted by conjugation or transformation into the desired strain of C. glutamicum. The conjugation method is described, for example, by Schäfer et al. (Applied and Environmental Microbiology 60, 756–759 (1994)). Transformation methods are described, for example, by Thierbach et al. (Applied Microbiology and Biotechnology 29, 356–362 (1988)), by Dunican and Shivnan (Bio/Technology 7, 1067–1070 (1989)) and by Tauch et al. (FEMS Microbiological Letters 123, 343–347 (1994)). After homologous recombination by means of a "cross over" occurrence, the resulting strain contains at least two copies of the gene concerned.

Moreover, apart from the plsC gene, it may be advantageous for the production of amino acids, particularly L-glutamate, to intensify or over-express one or more genes which encode enzymes of the biosynthesis route employed, of glycolysis, of anaplerosis, of the citric acid cycle or of amino acid export.

Thus, for the production of L-lysine, for example, one or more genes selected from the following group can be simultaneously enhanced, and in particular can be over-expressed or amplified:

the dapA gene which encodes dihydrodipicolinate synthase (EP-B 0 197 335), or the dapE gene which encodes succinyl diaminopimelate desuccinylase, or the lysC gene which encodes feed-back resistant aspartate kinase (Kalinowski et al. (1990), Molecular and General Genetics 224, 317–324), or the gap gene which encodes glyceraldehe-3-phosphate dehydrogenase (Eikmanns (1992), Journal of Bacteriology 174:6076–6086), or the tpi gene which encodes triose phosphate isomerase (Eikmanns (1992), Journal of Bacteriology 174:6076–6086), or the pgk gene which encodes 3-phosphoglycerate kinase (Eikmanns (1992), Journal of Bacteriology 174:6076–6086), or the pyc gene which encodes pyruvate carboxylase (DE-A-19831609), or simultaneously, the mqo gene which encodes malate-quinone oxidoreductase (Molenaar et al., European Journal of Biochemistry 254, 395–403 (1998)), or the lysE gene which encodes lysine export (DE-A-195 48 222).

Furthermore, for the production of L-glutamate, for example, one or more genes selected from the following group can be simultaneously enhanced, and in particular can be over-expressed or amplified:

the gdh gene which encodes glutamate-dehydrogenase (DE: 19907347.3), and/or the pyc gene which encodes pyruvate carboxylase (Peters-Wendisch et al.(1998), Microbiology 144: 915–927).

Moreover, for the production of L-lysine it may be advantageous if, in addition to the enhancement of the plsC gene:

the pck gene which encodes phosphoenol pyruvate carboxykinase (DE 199 50 409.1, DSM 13047) and/or the pgi gene which encodes glucose-6-phosphate isomerase (U.S. Ser. No. 09/396,478, DSM 12969)

is simultaneously attenuated.

Furthermore, for the production of L-glutamate it may be advantageous if, in addition to the enhancement of the plsC gene:

the odhA gene which encodes α-ketoglutarate dehydrogenase (WO 9534672 A1 951221*), or the dtsR1 gene which encodes DtsR1 protein (WO 952324 A1 950831*), or the dtsR2 gene which encodes DtsR2 protein (WO 9902692A A1 990121*), is simultaneously attenuated.

Moreover, for the production of amino acids, particularly L-lysine and L-glutamate, it may be advantageous if, in addition to the over-expression of the plsC gene, unwanted secondary reactions are suppressed (Nakayama: "Breeding of Amino Acid Producing Micro-organisms", in: Overproduction of Microbial Products, Krumphanzl, Sikyta, Vanek (Eds.), Academic Press, London, UK, 1982).

The microorganisms which are produced according to the invention can be cultivated batch-wise or continuously, e.g. by a batch process (batch cultivation) or by a fed batch process (feed process) or by a repeated fed batch process (repetitive feed process), for the purpose of producing amino acids, particularly L-glutamate. A review of known methods of cultivation is given in the textbook by Chmiel (Bioprozesstechnik 1. Einführung in die Bioverfahrenstechnik (Gustav Fischer Verlag, Stuttgart, 1991)) and in the textbook by Storhas (Bioreaktoren und periphere Einrichtungen (Vieweg Verlag, Brunswick/Wiesbaden, 1994)).

The culture medium which is used must fulfil the requirements of the strain concerned in a suitable manner. Descriptions of culture media for various microorganisms are given in the Handbook "Manual of Methods for General Bacteriology" published by the American Society for Bacteriology (Washington D.C., USA, 1981). Suitable sources of carbon include sugar and carbohydrates such as glucose, saccharose, lactose, fructose, maltose, molasses, starch and cellulose, oils and fats such as soya oil, sunflower oil, peanut oil and cocoa fat, fatty acids such as palmitic acid, stearic acid and linoleic acid, alcohols such as glycerol and ethanol, and organic acids such as acetic acid. These substances can be used individually or in admixture. Suitable sources of nitrogen include compounds which contain organic nitrogen, such as peptone, yeast extract, meat extract, malt extract, corn steep liquor, soya bean flour and urea, and inorganic compounds such as ammonium sulphate, ammonium chloride, ammonium phosphate, ammonium carbonate and ammonium nitrate. These sources of nitrogen can be used individually or in admixture. Phosphoric acid, potassium dihydrogen phosphate or dipotassium hydrogen phosphate, or the corresponding sodium-containing salts, can be used as sources of phosphorus. In addition, the culture medium must contain salts of metals such as magnesium sulphate or iron sulphate which are necessary for growth. Finally, essential growth promoting substances such as amino acids and vitamins can be used in addition to the aforementioned substances. Moreover, suitable precursors can be added to the culture medium. The aforementioned substances which are used can be added to the culture in the form of a single batch or can be supplied in a suitable manner during cultivation.

Basic compounds such as sodium hydroxide, potassium hydroxide, ammonia or aqueous ammonia, or acidic compounds such as phosphoric acid or sulphuric acid are used in a suitable manner in order to control the pH of the culture. Anti-foaming agents such polyglycol esters of fatty acids can be used to control the generation of foam. In order to maintain the stability of plasmids, suitable substances with a selective action, such as antibiotics, can be added to the medium. In order to maintain aerobic conditions, oxygen or oxygen-containing gas mixtures such as air are passed into the culture. The temperature of the culture normally ranges from 20° C. to 45° C. and is preferably 25° C. to 40° C. Cultivation is continued until a maximum of glutamate has been formed. This target is normally reached within 10 hours to 160 hours.

The following microorganism has been deposited on May 18, 2000 in the German Collection of Microorganisms and Cell Cultures (DSMZ, Brunswick, Germany) in accordance with the Budapest Convention:

Corynebacterium glutamicum strain DSM5715/pJC1plsC as DSM 13492.

The process according to the invention can be employed for the fermentative production of amino acids, particularly L-lysine and L-glutamate.

The numbers of base pairs are given as approximate values which can be obtained within the limits of reproducibility. The abbreviations and descriptions used have the following meanings:

Orf2,rep plasmid-coded replication origin C. glutamicum (of pHM1519)

plsC: 1-acyl-SN-glycerol-3-phosphate acyltransferase gene of C. glutamicum ATCC13032

Kan: kanamycin-resistant gene

XbaI: cleavage site of the restriction enzyme XbaI

PstI: cleavage site of the restriction enzyme PstI

XhoI: cleavage site of the restriction enzyme XhoI

SmaI: cleavage site of the restriction enzyme SmaI

BglII: cleavage site of the restriction enzyme BglII

EcoRI: cleavage site of the restriction enzyme EcoRI

Having generally described this invention, a further understanding can be obtained by reference to certain specific examples which are provided herein for purposes of illustration only, and are not intended to be limiting unless otherwise specified.

EXAMPLES

Example 1

Production of a genomic cosmid gene bank from Corynebacterium glutamicum ATCC 13032

Chromosomal DNA from Corynebacterium glutamicum ATCC13032 was isolated as described by Tauch et al. (1995, Plasmid 33:168–179) and was partially cleaved with the restriction enzyme Sau3AI (Amersham Pharmacia, Freiburg, Germany, product description Sau3AI, Code no. 27-0913-02). The DNA fragments were dephosphorylated with shrimp alkaline phosphatase (Roche Molecular Biochemicals, Mannheim, Germany, product description SAP, Code no. 1758250). The DNA of the cosmid vector SuperCos1 (Wahl et al. (1987) Proceedings of the National Academy of Sciences USA 84:2160–2164), purchased from Stratagene (La Jolla, USA, product description SuperCos1 cosmid vector Kit, Code no. 251301) was cleaved with the restriction enzyme XbaI (Amersham Pharmacia, Freiburg, Germany, product description XbaI, Code no. 27-0948-02) and was likewise dephosphorylated with shrimp alkaline phosphatase. The cosmid DNA was subsequently cleaved with the restriction enzyme BamHI (Amersham Pharmacia, Freiburg, Germany, product description BamHI, Code no. 27-0868-04). The cosmid DNA which was treated in this manner was mixed with the treated ATCC13032-DNA and the batch was treated with T4 DNA ligase (Amersham Pharmacia, Freiburg, Germany, product description T4-DNA-Ligase, Code no. 27-0870-04). The ligation mix was subsequently packed in phages with the aid of Gigapack II XL Packing Extract (Stratagene, La Jolla, USA, product description Gigapack II XL Packing Extract, Code no. 200217). In order to infect the E. coli strain NM554 (Raleigh et al. 1988, Nucleic Acid Research 16:1563–1575), the cells were taken up in mM MgSO$_4$ and were mixed with an aliquot of the phage suspension. Infection and titration of the cosmid bank were effected as described by Sambrook et al. (1989, Molecular Cloning: A Laboratory Manual, Cold Spring Harbor), with the cells being plated out on to LB agar (Lennox, 1955, Virology, 1:190) with 100 mg/l ampicillin. After incubation overnight at 37° C., recombinant individual clones were selected.

Example 2

Isolation and Sequencing of the plsC Gene

The cosmid DNA of a single colony was isolated using a Qiaprep Spin Miniprep Kit (Product No. 27106, Qiagen, Hilden, Germany) in accordance with the manufacturer's instructions and was partially cleaved with the restriction enzyme Sau3AI (Amersham Pharmacia, Freiburg, Germany, product description Sau3AI, Product No. 27-0913-02). The DNA fragments were dephosphorylated with shrimp alkaline phosphatase (Roche Molecular Biochemicals, Mannheim, Germany, product description SAP, Product No. 1758250). After separation by gel electrophoresis, cosmid fragments of the order of 1500 to 2000 bp were isolated using a QiaExII Gel Extraction Kit (Product No. 20021, Qiagen, Hilden, Germany). The DNA of the sequencing vector, pZero-1, purchased from Invitrogen (Groningen, Holland, product description Zero Background Cloning Kit, Product No. K2500-01) was cleaved with the restriction enzyme BamHI (Amersham Pharmacia, Freiburg, Germany, product description BamHI, Product No. 27-0868-04). Ligation of the cosmid fragments in the sequencing vector pZero-1 was effected as described by Sambrook et al. (1989, Molecular Cloning: A laboratory Manual, Cold Spring Harbor), the DNA mixture being incubated overnight with T4 ligase (Pharmacia Biotech, Freiburg, Germany). This ligation mix was subsequently transferred into E. coli strain DH5aMCR (Grant, 1990, Proceedings of the National Academy of Sciences U.S.A., 87:4645–4649) by means of electroporation (Tauch et al. 1994, FEMS Microbiol Letters, 123:343–7) and the electroporation batch was plated out on LB agar (Lennox, 1955, Virology, 1:190) with mg/l zeocin. The plasmid was prepared from the recombinant clone using a Biorobot 9600 (Product No. 900200, Qiagen, Hilden, Germany). Sequencing was effected by the dideoxy chain termination method of Sanger et al. (1977, Proceedings of the National Academy of Sciences U.S.A., 74:5463–5467) with modifications according to Zimmermann et al. (1990, Nucleic Acids Research, 18:1067). The "RR d-Rhodamine Terminator Cycle Sequencing Kit" of PE Applied Biosystems (Product No. 403044, Weiterstadt, Germany) was used for this purpose. Separation by gel electrophoresis and analysis of the sequencing reaction were effected in a "rotiphoresis NF acrylamide/bisacrylamide" gel (29:1) (Product No. A124.1, Roth, Karlsruhe, Germany), using the "ABI Prism 377" sequencing device of PE Applied Biosystems (Weiterstadt, Germany).

The raw sequence data which were obtained were subsequently processed using the Staden software package (1986, Nucleic Acids Research, 14:217–231) Version 97-0. The individual sequences of the pZero 1 derivatives were assembled to form a coherent contig. Computer-aided analysis was performed using the XNIP program (Staden, 1986, Nucleic Acids Research, 14:217–231). Further analyses were performed using "BLAST search programs" (Altschul et al., 1997, Nucleic Acids Research, 25:3389–3402), compared with the non-redundant databank of the National Center for Biotechnology Information (NCBI, Bethesda, Md., USA).

The nucleotide sequence obtained is illustrated in SEQ ID No. 1. Analysis of the nucleotide sequence showed the presence of an open reading frame comprising 735 base pairs, which was designated as the plsC gene. The plsC gene encodes a protein comprising 245 amino acids (SEQ ID No.2).

Example 3

Cloning the plsC Gene in the Vector pJC1

Chromosomal DNA from Corynebacterium glutamicum ATCC13032 was isolated as described by Tauch et al. (1995, Plasmid 33:168–179). A DNA fragment bearing the plsC gene was amplified by polymerase chain reaction. The following primers were used for this purpose:

```
5'-TGC TCT AGA GAT CGC TCG GTC AAC CAC TAT TCC-3'   (SEQ ID NO:3)

5'-TGC TCT AGA CAA CCG TCC GAC TCG ATG TAT GC-3'    (SEQ ID NO:4)
```

The primers illustrated were synthesised by MWG Biotech (Ebersberg, Germany) and the PCR reaction was carried out by the standard PCR method of Innis et al.(PCR protocol. A guide to methods and applications, 1990, Academic Press). The primers enabled amplification to be effected of a DNA fragment with a size of about 1193 bp and bearing the plsC gene of Corynebacterium glutamicum.

After separation by gel electrophoresis, the PCR fragment was isolated from the agarose gel using a QiaExII Gel Extraction Kit (Product No. 20021, Qiagen, Hilden, Germany).

The E. coli-C. glutamicum shuttle vector pJC1 (Cremer et al., 1990, Molecular and General Genetics 220: 478–480) was used as a vector. This plasmid was completely cleaved with the restriction enzyme BamHI, was treated with Klenow polymerase (Roche Diagnostics GmbH, Mannheim, Germany) and was subsequently dephosphorylated with shrimp alkaline phosphatase (Roche Diagnostics GmbH, Mannheim, Germany, product description SAP, Product No. 1758250).

The plsC fragment obtained in this manner was mixed with the prepared vector pJC1 and was ligated with the aid of a SureClone Ligation Kit (Amersham Pharmacia Biotech, Uppsala, Sweden) according to the manufacturer's instructions. The ligation batch was transformed in the *E. coli* strain DH5α (Hanahan, in: DNA cloning. A practical approach. Vol. 1. IRL Press, Oxford, Washington D.C., USA). Plasmid-bearing cells were selected by plating out the transformation batch on LB agar (Lennox, 1955, Virology, 1:190) with mg/l kanamycin. After incubation overnight at 37° C., recombinant individual clones were selected. Plasmid DNA was isolated from a transformant using a Qiaprep Spin Miniprep Kit (Product No. 27106, Qiagen, Hilden, Germany) according to the manufacturer's instructions and was cleaved with the restriction enzyme XbaI in order to investigate the plasmid by subsequent agarose gel electrophoresis. The plasmid obtained was designated as pJC1plsC.

Example 4

Transformation of the Strains ATCC13032 and DSM5715 with the Plasmid pJC1plsC

The *C. glutamicum* strains ATCC13032 and DSM5715 were transformed with the plasmid pJC1plsC using the electrophoration method described by Liebl et al. (FEMS Microbiology Letters, 53:299–303 (1989)). The transformants were selected on LBHIS agar consisting of 18.5 g/l brain-heart infusion bouillon, 0.5 M sorbitol, g/l bacteriological trypton, 2.5 g/l bacteriological yeast extract, g/l NaCl and 18 g/l bacteriological agar which was supplemented with mg/l kanamycin. Incubation was effected for 2 days at 33° C.

Plasmid DNA was isolated from each transformant by the usual methods (Peters-Wendisch et al., 1998, Microbiology, 144, 915–927), was cut with the restriction endonuclease XbaI and the plasmid was investigated by subsequent agarose gel electrophoresis. The strains obtained were designated as ATCC13032/pJC1plsC and DSM5715/pJC1plsC.

Example 5

Production of L-glutamate Using the Strain ATCC13032/pJC1plsC

The *C. glutamicum* strain ATCC13032/pJC1plsC which was obtained in Example 4 was cultivated in a nutrient medium suitable for the production of glutamate, and the glutamate content in the culture supernatant was determined.

For this purpose, the strain was first incubated on an agar plate with the corresponding antibiotic (brain-heart agar with kanamycin (50 mg/l)) for 24 hours at 33° C. A preliminary culture was inoculated with this agar plate culture (10 ml medium in an 100 ml Erlenmeyer flask). The complete medium CgIII (2.5 g/l NaCl, 10 g/l bacteriological peptone, 10 g/l bacteriological yeast extract, pH 7.4, 20 g/l glucose (autoclaved separately)) was used as the medium for the preliminary culture.

Kanamycin (25 mg/l) was added to the latter. The preliminary culture was incubated for 16 hours at 33° C., at 240 rpm on a shaker. A main culture was inoculated with this preliminary culture so that the initial OD (660 nm) of the main culture was 0.1. The medium CgXII was used for the main culture.

After preliminary cultivation in CgIII medium(Keilhauer et al. 1993, Journal of Bacteriology 175:5595–5603), the strain ATCC13032/pJC1plsC was cultivated in CgXII production medium (Keilhauer et al. 1993, Journal of Bacteriology 175:5595–5603). 4% glucose and mg/l kanamycin sulphate were added.

To induce glutamate formation, 20 g Tween (P-1629, Sigma-Aldrich, Deisenhofen, Germany) plus 80 ml water were mixed and autoclaved. About 4 hours after inoculation, 75 μl of this Tween solution was added to the culture and cultivation was continued.

Cultivation was effected in a volume of 10 ml in a 100 ml Erlenmeyer flask fitted with baffles. Kanamycin (25 mg/l) was added. Cultivation was conducted at 33° C. and 80% atmospheric humidity.

After 48 hours, the OD was determined at a measuring wavelength of 660 nm using a Biomek 1000 (Beckmann Instruments GmbH, Munich). The quantity of glutamate formed was determined using an amino acid analyser supplied by Eppendorf-BioTronik (Hamburg, Germany), by ion exchange chromatography and subsequent derivative formation using ninhydrin as a detector.

The results of the experiment are given in Table 1.

TABLE 1

| Strain | OD (660 nm) | Glutamate-HCl |
| --- | --- | --- |
| ATCC13032/pJC1plsC | 14.7 | 110 |
| ATCC13032 | 13.8 | 94 |

Example 6

Production of L-lysine

The *C. glutamicum* strain DSM5715/pJC1plsC obtained in Example 4 was cultivated in a nutrient medium suitable for the production of lysine, and the lysine content in the culture supernatant was determined.

For this purpose, the strain was first incubated on an agar plate with the corresponding antibiotic (brain-heart agar with kanamycin (50 mg/l)) for 24 hours at 33° C. A preliminary culture was inoculated with this agar plate culture (ml medium in an 100 ml Erlenmeyer flask). The complete medium CgIII (2.5 g/l NaCl, 10 g/l bacteriological peptone, 10 g/l bacteriological yeast extract, pH 7.4, 20 g/l glucose (autoclaved separately)) was used as the medium for the preliminary culture. Kanamycin (25 mg/l) was added thereto. The preliminary culture was incubated for 16 hours at 33° C., at 240 rpm on a shaker. A main culture was inoculated with this preliminary culture so that the initial OD (660 nm) of the main culture was 0.1. The medium MM was used for the main culture.

| Medium MM | |
| --- | --- |
| CSL (corn steep liquor) | 5 g/l |
| MOPS (morpholinopropanesulphonic acid) | 20 g/l |
| glucose (autoclaved separately) | 50 g/l |
| $(NH_4)_2SO_4$ | 25 g/l |
| $KH_2PO_4$ | 0.1 g/l |
| $MgSO_4 * 7H_2O$ | 1.0 g/l |
| $CaCl_2 * 2H_2O$ | 10 mg/l |
| $FeSO_4 * 7H_2O$ | 10 mg/l |
| $MnSO_4 * H_2O$ | 5.0 mg/l |
| Biotin (filtered under sterile conditions) | 0.3 mg/l |
| thiamine*HCl (filtered under sterile conditions) | 0.2 mg/l |

15

-continued

| Medium MM | |
|---|---|
| L-leucine | 0.1 g/l |
| CaCO₃ | 25 g/l |

The CSL, the MOPS and the salt solution were adjusted to pH 7 with aqueous ammonia and were autoclaved. The sterile substrate and vitamin solutions were then added, together with dried, autoclaved CaCO₃.

Cultivation was effected in a volume of ml in a 100 ml Erlenmeyer flask fitted with baffles. Kanamycin (mg/l) was added. Cultivation was conducted at 33° C. and 80% atmospheric humidity.

After 72 hours, the OD was determined at a measuring wavelength of 660 nm using a Biomek 1000 (Beckmann Instruments GmbH, Munich). The quantity of lysine formed was determined using an amino acid analyser supplied by Eppendorf-BioTronik (Hamburg, Germany), by ion exchange chromatography and subsequent derivative formation using ninhydrin as a detector.

The results of the experiment are given in Table 2

16

TABLE 2

| Strain | OD (660 nm) | Lysine-HCl |
|---|---|---|
| DSM5715/pJC1plsC | 7.53 | 14.84 |
| DSM5715 | 7.57 | 13.52 |

The foreign priority document DE 100 32 173.9 filed Jul. 1, 2000 is herein incorporated by reference.

Obviously, numerous modifications and variations on the present invention are possible in light of the above teachings. It is therefore to be understood that within the scope of the appended claims, the invention may be practiced otherwise than as specifically described herein.

What is claimed is:

1. An isolated polynucleotide consisting of:
   a sequence that encodes the 1-acyl-SN-glycerol-3-phosphate acyltransferase of SEQ ID NO: 2 or a fragment of SEQ ID NO: 2 having 1-acyl-SN-glycerol-3-phosphate acyltransferase activity, and
   optionally (a) a polynucleotide encoding one or more heterologous protein(s) or (b) one or more nucleotide sequences selected from the group consisting of a promoter, a ribosome binding site or a regulatory region, or both (a) and (b).

2. The isolated polynucleotide of claim 1 comprising a polynucleotide encoding one or more heterologous protein(s).

3. The isolated polynucleotide of claim 1 comprising one or more nucleotide sequences selected from the group consisting of a promoter, a ribosome binding site or a regulatory region.

4. A vector comprising the isolated polynucleotide sequence of claim 1.

5. A host cell comprising the isolated polynucleotide sequence of claim 1.

6. The host cell of claim 5 that is a coryneform bacterium.

7. The coryneform bacterium of claim 6 that is selected from the group consisting of *Corynebacterium glutamicum, Corynebacterium acetoglutamicum, Corynebacterium thermoaminogenes, Corynebacterium melassecola, Brevibacterium flavum, Brevibacterium lactofermentum,* and *Brevibacterium divaricatum*.

8. A method for making a polypeptide having 1-acyl-SN-glycerol-3-phosphate acyltransferase activity comprising:
   culturing the host cell of claim 5 for a time and under conditions suitable for the expression of a polypeptide having 1-acyl-SN-glycerol-3-phosphate acyltransferase activity and recovering or collecting said polypeptide.

9. An isolated polynucleotide that is the full complement of the polynucleotide sequence of claim 1.

10. An isolated polynucleotide that comprises SEQ ID NO: 1.

11. The isolated polynucleotide of claim 10 consisting of SEQ ID NO: 1.

12. An isolated polynucleotide consisting of SEQ ID NO: 1 or a fragment thereof that encodes a polypeptide having 1-acyl-SN-glycerol-3-phosphate acyltransferase activity and optionally (a) a polynucleotide encoding one or more heterologous protein(s) or (b) one or more nucleotide sequences selected from the group consisting of a promoter, a ribosome binding site or a regulatory region, or both (a) and (b).

13. The isolated polynucleotide of claim 12 consisting of nucleotides 323 to 1057 of SEQ ID NO: 1 or a fragment thereof encoding a protein having 1-acyl-SN-glycerol-3-phosphate acyltransferase activity.

14. A vector comprising the isolated polynucleotide sequence of claim 12.

15. A host cell comprising the isolated polynucleotide sequence of claim 12.

16. The host cell of claim 15 that is a coryneform bacterium.

17. The coryneform bacterium of claim 16 that is selected from the group consisting of *Corynebacterium glutamicum, Corynebacterium acetoglutamicum, Corynebacterium thermoaminogenes, Corynebacterium melassecola, Brevibacterium flavum, Brevibacterium lactofermentum,* and *Brevibacterium divaricatum.*

18. A method for making a polypeptide having 1-acyl-SN-glycerol-3-phosphate acyltransferase activity comprising:
culturing the host cell of claim 15 for a time and under conditions suitable for the expression of a polypeptide having 1-acyl-SN-glycerol-3-phosphate acyltransferase activity and recovering or collecting said polypeptide.

19. An isolated polynucleotide that is the full complement of the polynucleotide of claim 12.

20. An isolated polynucleotide consisting of:
a polynucleotide sequence that is at least 70% identical to SEQ ID NO: 1 or a fragment thereof and which consists of a sequence that encodes a polypeptide having 1-acyl-SN-glycerol-3-phosphate acyltransferase activity, or
a polynucleotide sequence that hybridizes under stringent conditions to SEQ ID NO: 1 and which consists of a sequence that encodes a polypeptide having 1-acyl-SN-glycerol-3-phosphate acyltransferase activity, wherein said stringent conditions comprise washing in 5×SSC at a temperature ranging from 50° C. to 68° C.; and
optionally (a) a polynucleotide encoding one or more heterologous protein(s) or (b) one or more nucleotide sequences selected from the group consisting of a promoter, a ribosome binding site or a regulatory region, or both (a) and (b).

21. The isolated polynucleotide of claim 20 that is at least 70% identical to SEQ ID NO: 1 and that encodes a polypeptide having 1-acyl-SN-glycerol-3-phosphate acyltransferase activity.

22. The isolated polynucleotide of claim 20 that is at least 80% identical SEQ ID NO: 1 and that encodes a polypeptide having 1-acyl-SN-glycerol-3-phosphate acyltransferase activity.

23. The isolated polynucleotide of claim 20 that is at least 90% identical SEQ ID NO: 1 and that encodes a polypeptide having 1-acyl-SN-glycerol-3-phosphate acyltransferase activity.

24. The isolated polynucleotide of claim 20 that hybridizes under stringent conditions to SEQ ID NO: 1 and consists of a sequence that encodes a polypeptide having 1-acyl-SN-glycerol-3-phosphate acyltransferase activity, wherein said stringent conditions comprise washing in 5×SSC at a temperature ranging from 50° C. to 68° C.

25. The isolated polynucleotide of claim 20 that comprises (a) a polynucleotide encoding one or more heterologous protein(s), (b) a polynucleotide sequence selected from the group consisting of a promoter, a ribosome binding site and a regulatory region, or both (a) and (b).

26. A vector comprising the isolated polynucleotide sequence of claim 20.

27. A host cell comprising the isolated polynucleotide sequence of claim 20.

28. The host cell of claim 27 that is a coryneform bacterium.

29. The coryneform bacterium of claim 28 that is selected from the group consisting of *Corynebacterium glutamicum, Corynebacterium acetoglutamicum, Corynebacterium thermoaminogenes, Corynebacterium melassecola, Brevibacterium flavum, Brevibacterium lactofermentum,* and *Brevibacterium divaricatum.*

30. A Coryneform bacterium comprising an enhanced plsC gene that comprises the isolated polynucleotide sequence of claim 20.

31. A Corynebacterium glutamicum DSM 13492.

32. A method for making a polypeptide having 1-acyl-SN-glycerol-3-phosphate acyltransferase activity comprising: culturing the host cell of claim 27 for a time and under conditions suitable for the expression of a polypeptide having 1-acyl-SN-glycerol-3-phosphate acyltransferase activity and recovering or collecting said polypeptide.

33. The full complement of the isolated polynucleotide sequence of claim 20.

34. A process for producing one or more L-amino acid(s) comprising culturing the host cell of claim 29 for a time and under conditions suitable for production of an L-amino acid, and collecting the L-amino acid.

35. The process of claim 34, wherein said L-amino acid is L-lysine.

36. The process of claim 34, wherein said L-amino acid is L-glutamate.

37. The process of claim 34, wherein the host cell further comprises at least one gene whose expression is enhanced, wherein said gene is selected from the group consisting of dapA, dapE, lysC, gap, tpi, pgk, pyc, mqo, and lys E.

38. The process of claim 34, wherein said L-amino acid is L-glutamate and the host cell further comprises at least one gene whose expression is enhanced, wherein said gene is selected from the group consisting of gdh, pyc, odhA, dtsR1 and dtsR2.

39. The process of claim 34, wherein said L-amino acid is L-lysine and the host cell further comprises an attenuated pck gene, pgi gene, or both pck and pgi genes.

40. A process for producing one or more L-amino acid(s) comprising:
culturing the host cell of claim 5 for a time and under conditions suitable for the production of an L-amino acid and collecting the L-amino acid.

41. The process of claim 40, wherein said L-amino acid is L-lysine.

42. The process of claim 40, wherein said L-amino acid is L-glutamate.

43. The process of claim 40, wherein the host cell further comprises at least one gene whose expression is enhanced, wherein said gene is selected from the group consisting of dapA, dapE, lysC, gap, tpi, pgk, pyc, mqo, and lys E.

44. The process of claim 40, wherein said L-amino acid is L-glutamate and the host cell further comprises at least one gene whose expression is enhanced, wherein said gene is selected from the group consisting of gdh, pyc, odhA, dtsR1 and dtsR2.

45. The process of claim 40, wherein said L-amino acid is L-lysine and the host cell further comprises an attenuated pck gene, pgi gene, or both pck and pgi genes.

46. A process for producing one or more L-amino acid(s) comprising culturing *Corynebacterium glutamicum* DSM 13492 in a medium suitable for production of an L-amino acid and recovering or collecting the L-amino acid.

47. The process of claim 46, wherein said L-amino acid is L-lysine.

48. The process of claim 46, wherein said L-amino acid is L-glutamate.

49. The process of claim 46, wherein the host cell further comprises at least one gene whose expression is enhanced, wherein said gene is selected from the group consisting of dapA, dapE, lysC, gap, tpi, pgk, pyc, mqo, and lys E.

50. The process of claim 46, wherein said L-amino acid is L-glutamate and the host cell further comprises at least one gene whose expression is enhanced, wherein said gene is selected from the group consisting of gdh, pyc, odhA, dtsR1 and dtsR2.

51. The process of claim 46, wherein said L-amino acid is L-lysine and the host cell further comprises an attenuated pck gene, pgi gene, or both pck and pgi genes.

* * * * *

SEQUENCE LISTING

<160> NUMBER OF SEQ ID NOS: 4

<210> SEQ ID NO 1
<211> LENGTH: 1211
<212> TYPE: DNA
<213> ORGANISM: Corynebacterium glutamicum
<220> FEATURE:
<221> NAME/KEY: CDS
<222> LOCATION: (323)..(1057)

<400> SEQUENCE: 1

```
tgctctagag atcgctcggt caaccactat tccacccgca tcgtcggcgc aggatatcgc      60
cctttggcac gcgttgccac agctcagttg ggtgcggatg ctggcatgat cggtgtcgct     120
gatctagctc gacgctctgt agtggaagcc aactaggtgt ttttcggtgg gctgcgatga     180
cgcatgtcca ccaaaagagc cacccttaa agaaattaaa aagtggtttt ggtagcttcg      240
cagcaaaata cacatcgtgg gtaacgtatt cttagaagtt cctacagcag taaagcgcga     300 agaagggta aacccaaaca tc atg aaa aac aac tgg tat cgg ctt ttc aag      352
                         Met Lys Asn Asn Trp Tyr Arg Leu Phe Lys
                           1               5                  10 tat gtg cta att ggc ccg ttt ttg cgt gtg tac aac cgc ccg gag atc       400
Tyr Val Leu Ile Gly Pro Phe Leu Arg Val Tyr Asn Arg Pro Glu Ile
                15                  20                  25 gaa ggc aaa gaa aac atc cct gca gaa ggt gcc gcg atc atg gcg tcc       448
Glu Gly Lys Glu Asn Ile Pro Ala Glu Gly Ala Ala Ile Met Ala Ser
             30                  35                  40 aac cac gaa gca gtg atg gat tcc ttt tat ttt ccc ctg ctg tgc cca       496
Asn His Glu Ala Val Met Asp Ser Phe Tyr Phe Pro Leu Leu Cys Pro
         45                  50                  55 cgg cag ctg acc ttc cca gcg aag gcc gaa tac ttc aca tca cca ggt       544
Arg Gln Leu Thr Phe Pro Ala Lys Ala Glu Tyr Phe Thr Ser Pro Gly
     60                  65                  70 att aaa ggc aag atg cag aag tgg ttt ttt act tct gtg ggg caa gta       592
Ile Lys Gly Lys Met Gln Lys Trp Phe Phe Thr Ser Val Gly Gln Val
 75                  80                  85                  90 ccc ctg gac cgc acc gca gat aat gcc atg gat tct ttg atg aat acc       640
Pro Leu Asp Arg Thr Ala Asp Asn Ala Met Asp Ser Leu Met Asn Thr
                 95                 100                 105
```

```
gcc aaa atg gtg ctg gat cgg gga gac ctc ttc ggt att tac cct gaa         688
Ala Lys Met Val Leu Asp Arg Gly Asp Leu Phe Gly Ile Tyr Pro Glu
        110                 115                 120 gga tct cgt tcg ccc gat ggt cgc atc tac aag ggc aaa acc gga atg         736
Gly Ser Arg Ser Pro Asp Gly Arg Ile Tyr Lys Gly Lys Thr Gly Met
            125                 130                 135 gcc tat gtt gcg atg gaa act ggt acg aca gtt atc ccc gtt gcc atg         784
Ala Tyr Val Ala Met Glu Thr Gly Thr Thr Val Ile Pro Val Ala Met
140                 145                 150 att ggc agc cgg gac gcg aac cct atc gga agt tgg ttt ccg aaa ccc         832
Ile Gly Ser Arg Asp Ala Asn Pro Ile Gly Ser Trp Phe Pro Lys Pro
155                 160                 165                 170 gca aaa gtc agg atc aag gta gga agc cca att gat ccc ctc gca ttc         880
Ala Lys Val Arg Ile Lys Val Gly Ser Pro Ile Asp Pro Leu Ala Phe
                175                 180                 185 gtc aaa gaa cat ggg ttg aag cct gga acc tac gaa gca gcg cgc aag         928
Val Lys Glu His Gly Leu Lys Pro Gly Thr Tyr Glu Ala Ala Arg Lys
                190                 195                 200 ctg aca gat cac gtt atg ttc att ctt gct gat ctc act ggt cag ccg         976
Leu Thr Asp His Val Met Phe Ile Leu Ala Asp Leu Thr Gly Gln Pro
            205                 210                 215 tat gtt gat gcg tac tct aaa gat gtg aaa aac gct ctg gag gaa gga        1024
Tyr Val Asp Ala Tyr Ser Lys Asp Val Lys Asn Ala Leu Glu Glu Gly
220                 225                 230 aaa gga tac ccg gag ggc aca gct cct tca cag taatcgggtc ttttctgtta      1077
Lys Gly Tyr Pro Glu Gly Thr Ala Pro Ser Gln
235                 240                 245 aaaaccttgg ggttttttgtg tgagtctttt cgtattcggg tggcagaacg gtatggttgt     1137
accggttagg cttcaagatt taactaattg ttaatctttt tggcatacat cgagtcggac     1197
ggttgtctag agca                                                        1211

<210> SEQ ID NO 2
<211> LENGTH: 245
<212> TYPE: PRT
<213> ORGANISM: Corynebacterium glutamicum

<400> SEQUENCE: 2

Met Lys Asn Asn Trp Tyr Arg Leu Phe Lys Tyr Val Leu Ile Gly Pro
1               5                   10                  15

Phe Leu Arg Val Tyr Asn Arg Pro Glu Ile Glu Gly Lys Glu Asn Ile
            20                  25                  30

Pro Ala Glu Gly Ala Ala Ile Met Ala Ser Asn His Glu Ala Val Met
        35                  40                  45

Asp Ser Phe Tyr Phe Pro Leu Leu Cys Pro Arg Gln Leu Thr Phe Pro
    50                  55                  60

Ala Lys Ala Glu Tyr Phe Thr Ser Pro Gly Ile Lys Gly Lys Met Gln
65                  70                  75                  80

Lys Trp Phe Phe Thr Ser Val Gly Gln Val Pro Leu Asp Arg Thr Ala
                85                  90                  95

Asp Asn Ala Met Asp Ser Leu Met Asn Thr Ala Lys Met Val Leu Asp
            100                 105                 110

Arg Gly Asp Leu Phe Gly Ile Tyr Pro Glu Gly Ser Arg Ser Pro Asp
        115                 120                 125

Gly Arg Ile Tyr Lys Gly Lys Thr Gly Met Ala Tyr Val Ala Met Glu
    130                 135                 140

Thr Gly Thr Thr Val Ile Pro Val Ala Met Ile Gly Ser Arg Asp Ala
145                 150                 155                 160
```

```
Asn Pro Ile Gly Ser Trp Phe Pro Lys Pro Ala Lys Val Arg Ile Lys
            165                 170                 175

Val Gly Ser Pro Ile Asp Pro Leu Ala Phe Val Lys Glu His Gly Leu
            180                 185                 190

Lys Pro Gly Thr Tyr Glu Ala Ala Arg Lys Leu Thr Asp His Val Met
            195                 200                 205

Phe Ile Leu Ala Asp Leu Thr Gly Gln Pro Tyr Val Asp Ala Tyr Ser
        210                 215                 220

Lys Asp Val Lys Asn Ala Leu Glu Glu Gly Lys Gly Tyr Pro Glu Gly
225                 230                 235                 240

Thr Ala Pro Ser Gln
                245

<210> SEQ ID NO 3
<211> LENGTH: 33
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 3
tgctctagag atcgctcggt caaccactat tcc                                33

<210> SEQ ID NO 4
<211> LENGTH: 32
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 4
tgctctagac aaccgtccga ctcgatgtat gc                                 32
```